United States Patent
Mon

(10) Patent No.: US 8,221,414 B2
(45) Date of Patent: Jul. 17, 2012

(54) CATHETER

(75) Inventor: John Mon, Silver Spring, MD (US)

(73) Assignee: Boston Scientific Corporation, Natick, MA (US)

( * ) Notice: Subject to any disclaimer, the term of this patent is extended or adjusted under 35 U.S.C. 154(b) by 0 days.

(21) Appl. No.: 12/902,636

(22) Filed: Oct. 12, 2010

(65) Prior Publication Data

US 2011/0028886 A1    Feb. 3, 2011

Related U.S. Application Data

(63) Continuation of application No. 10/436,500, filed on May 13, 2003, now Pat. No. 7,837,720, and a continuation-in-part of application No. 10/247,747, filed on Sep. 20, 2002, now Pat. No. 6,788,977, which is a continuation-in-part of application No. 09/954,194, filed on Sep. 18, 2001, now Pat. No. 6,958,075, which is a continuation-in-part of application No. 09/597,234, filed on Jun. 20, 2000, now Pat. No. 6,477,426.

(51) Int. Cl.
*A61B 18/18* (2006.01)

(52) U.S. Cl. ............... 606/41; 606/42; 606/49; 607/96; 607/98; 607/101; 604/96.01; 604/213; 604/507

(58) Field of Classification Search ........... 604/96.01, 604/213, 507; 606/41–49; 607/96, 98–101
See application file for complete search history.

(56) References Cited

U.S. PATENT DOCUMENTS

| | | |
|---|---|---|
| 3,125,096 A | 3/1964 | Antiles et al. |
| 3,895,639 A | 7/1975 | Rodler |
| 4,589,423 A | 5/1986 | Turner |
| 4,709,698 A | 12/1987 | Johnston et al. |
| 4,754,752 A | 7/1988 | Ginsburg et al. |
| 4,799,479 A | 1/1989 | Spears |
| 4,813,429 A | 3/1989 | Eshel et al. |

(Continued)

FOREIGN PATENT DOCUMENTS

WO    WO-93/08876 A1    5/1993

(Continued)

OTHER PUBLICATIONS

England et al., "Dielectric Properties of the Human Body in the Microwave Region of the Spectrum", Nature, vol. 163, pp. 487-488, Mar. 26, 1949.

(Continued)

*Primary Examiner* — Aaron Roane
(74) *Attorney, Agent, or Firm* — Brown Rudnick LLP

(57) ABSTRACT

An apparatus for treatment of tissue within a body requiring thermotherapy includes a catheter to be inserted into a bodily conduit, an energy-emitting source disposed within the catheter, a compression balloon surrounding the energy-emitting source where the compression balloon has an inflated diameter that is greater than that of the bodily conduit in a relaxed state and an outside surface of the balloon is coated with one of gene modifiers and drug or medication, and means for activating the energy-emitting source to radiate energy to heat the drug-coated compression balloon and tissue to be treated whereby the heated drug-coated compression balloon effectively delivers the one of the gene modifiers and drug or medication to a target area of the diseased tissue. In addition, methods for using the above apparatus to treat diseased tissue are disclosed.

7 Claims, 4 Drawing Sheets

U.S. PATENT DOCUMENTS

| | | |
|---|---|---|
| 4,955,377 A | 9/1990 | Lennox et al. |
| 4,998,933 A | 3/1991 | Eggers et al. |
| 5,007,437 A | 4/1991 | Sterzer |
| 5,019,075 A | 5/1991 | Spears et al. |
| 5,035,694 A | 7/1991 | Kasprzyk et al. |
| 5,061,267 A | 10/1991 | Zeiher |
| 5,094,854 A | 3/1992 | Ogawa et al. |
| 5,114,423 A | 5/1992 | Kasprzyk et al. |
| 5,151,100 A | 9/1992 | Abele et al. |
| 5,190,540 A | 3/1993 | Lee |
| 5,190,761 A | 3/1993 | Liburdy |
| 5,191,883 A | 3/1993 | Lennox et al. |
| 5,207,672 A | 5/1993 | Roth et al. |
| 5,226,430 A | 7/1993 | Spears et al. |
| 5,233,994 A | 8/1993 | Shmulewitz |
| 5,234,004 A | 8/1993 | Hascoet et al. |
| 5,251,645 A | 10/1993 | Fenn |
| 5,257,977 A | 11/1993 | Eshel |
| 5,292,321 A | 3/1994 | Lee |
| 5,314,466 A | 5/1994 | Stern et al. |
| 5,330,518 A | 7/1994 | Neilson et al. |
| 5,344,398 A | 9/1994 | Hara |
| 5,368,591 A | 11/1994 | Lennox et al. |
| 5,370,608 A | 12/1994 | Sahota et al. |
| 5,413,588 A | 5/1995 | Rudie et al. |
| 5,417,653 A | 5/1995 | Sahota et al. |
| 5,417,689 A | 5/1995 | Fine |
| 5,431,648 A | 7/1995 | Lev |
| 5,441,532 A | 8/1995 | Fenn |
| 5,464,437 A | 11/1995 | Reid et al. |
| 5,464,445 A | 11/1995 | Rudie et al. |
| 5,480,417 A | 1/1996 | Hascoet et al. |
| 5,496,271 A | 3/1996 | Burton et al. |
| 5,499,994 A | 3/1996 | Tihon et al. |
| 5,509,929 A | 4/1996 | Hascoet et al. |
| 5,520,684 A | 5/1996 | Imran |
| 5,540,655 A | 7/1996 | Edwards et al. |
| 5,540,679 A | 7/1996 | Fram et al. |
| 5,540,737 A | 7/1996 | Fenn |
| 5,545,137 A | 8/1996 | Rudie et al. |
| 5,549,559 A | 8/1996 | Eshel |
| 5,571,153 A | 11/1996 | Wallsten |
| 5,575,811 A | 11/1996 | Reid et al. |
| 5,578,008 A | 11/1996 | Hara |
| 5,620,480 A | 4/1997 | Rudie |
| 5,624,392 A | 4/1997 | Saab |
| 5,643,335 A | 7/1997 | Reid et al. |
| 5,653,692 A | 8/1997 | Masterson et al. |
| 5,688,269 A | 11/1997 | Newton et al. |
| 5,755,754 A | 5/1998 | Rudie et al. |
| 5,775,338 A | 7/1998 | Hastings |
| 5,810,767 A | 9/1998 | Klein |
| 5,810,888 A | 9/1998 | Fenn |
| 5,827,269 A | 10/1998 | Saadat |
| 5,843,144 A | 12/1998 | Rudie et al. |
| 5,879,347 A | 3/1999 | Saadat |
| 5,891,134 A | 4/1999 | Goble et al. |
| 5,902,268 A | 5/1999 | Saab |
| 5,916,240 A | 6/1999 | Rudie et al. |
| 5,916,241 A | 6/1999 | Rudie et al. |
| 5,931,860 A | 8/1999 | Reid et al. |
| 5,957,917 A | 9/1999 | Doiron et al. |
| 5,987,360 A | 11/1999 | McGrath et al. |
| 5,992,419 A | 11/1999 | Sterzer et al. |
| 6,006,755 A | 12/1999 | Edwards |
| 6,102,929 A | 8/2000 | Conway et al. |
| 6,123,083 A | 9/2000 | McGrath et al. |
| 6,129,726 A | 10/2000 | Edwards et al. |
| 6,139,571 A | 10/2000 | Fuller et al. |
| 6,190,355 B1 | 2/2001 | Hastings |
| 6,197,309 B1 | 3/2001 | Wheeler |
| 6,200,573 B1 | 3/2001 | Locke |
| 6,200,598 B1 | 3/2001 | Needham |
| 6,224,590 B1 | 5/2001 | Daikuzono |
| 6,224,591 B1 | 5/2001 | Claren et al. |
| 6,230,060 B1 * | 5/2001 | Mawhinney .................. 607/101 |
| 6,245,062 B1 | 6/2001 | Berube et al. |
| RE37,315 E | 8/2001 | Lev |
| 6,287,320 B1 | 9/2001 | Slepian |
| 6,366,818 B1 | 4/2002 | Bolmsjo |
| 6,409,716 B1 | 6/2002 | Sahatjian et al. |
| 6,433,147 B1 | 8/2002 | Ni et al. |
| 6,447,505 B2 | 9/2002 | McGovern et al. |
| 6,477,426 B1 | 11/2002 | Fenn et al. |
| 6,524,274 B1 | 2/2003 | Rosenthal et al. |
| 6,540,771 B2 | 4/2003 | Dobak, III et al. |
| 6,567,705 B1 | 5/2003 | Stokes et al. |
| 6,617,864 B2 | 9/2003 | Inoue et al. |
| 6,640,139 B1 | 10/2003 | Ueberle |
| 6,682,555 B2 | 1/2004 | Cioanta et al. |
| 6,743,779 B1 * | 6/2004 | Unger et al. .................. 514/44 R |
| 6,788,977 B2 | 9/2004 | Fenn et al. |
| 6,958,075 B2 | 10/2005 | Mon et al. |
| 7,811,313 B2 | 10/2010 | Mon et al. |
| 7,833,220 B2 | 11/2010 | Mon et al. |
| 2001/0001314 A1 | 5/2001 | Davison et al. |
| 2002/0151844 A1 | 10/2002 | Yang et al. |
| 2003/0055470 A1 | 3/2003 | Mon et al. |
| 2003/0069619 A1 | 4/2003 | Fenn et al. |
| 2003/0229384 A1 | 12/2003 | Mon |

FOREIGN PATENT DOCUMENTS

| | | |
|---|---|---|
| WO | WO-93/09845 A1 | 5/1993 |
| WO | WO-99/07315 A1 | 2/1999 |
| WO | WO-99/58194 A1 | 11/1999 |
| WO | 00/48518 A1 | 8/2000 |
| WO | WO-00/45758 A1 | 8/2000 |
| WO | 01/98764 A2 | 12/2001 |

OTHER PUBLICATIONS

Duck, "Physical Properties of Tissue, A Comprehensive Reference Book", Academic Press Inc., San Diego, CA, pp. 320-321, 1990.

Foster et al., "Dielectric Properties of Tumor and Normal Tissues at Radio through Microwave Frequencies", Journal of Microwave Power, 16 (2), pp. 107-119, 1981.

Valdagni, M.D. et al., "Report of Long-term Follow-up in a Randomized Trial Comparing Radiation Therapy and Radiation Therapy Plus Hyperthermia to Metastatic Lymphnodes in Stage IV Head and Neck Patients", Int. J. Radiation Oncology Biol. Phys., vol. 28, No. 1, pp. 163-169, 1993.

Overgaard et al., "Hyperthermia as an Adjuvant to Radiation Therapy of Recurrent or Metastatic Malignant Melanoma. A Multicentre Randomized Trial by the European Society for Hyperthermic Oncology", Int. J. Hyperthermia, vol. 12, No. 1, pp. 3-20, 1996.

Hall, "Radiobiology for the Radiologist", J.B. Lippincott Company, Philadelphia, pp. 262-263, 1994.

Perez et al.,"Principles and Practice of Radiation Oncology", J.B. Lippincott Company, Philadelphia, second edition, pp. 396-397, 1994.

Sapareto et al., "Thermal Dose Determination in Cancer Therapy", Int. J. Radiation Oncology Biol. Phys., vol. 10, No. 6, pp. 787-800, Jun. 1984.

von Hippel et al., "Dielectric Analysis of Biomaterials", Massachusetts Institute of Technology, pp. ai-ii, and 1-20, Oct. 1973.

Bassen et al., "Evaluation of an Implantable Electric-Field Probe within Finite Simulated Tissues", American Geophysical Union, vol. 12, No. 6(s), pp. 15-25, Nov.-Dec. 1977.

Samaras et al., "Production of Controlled Hyperthermal Fields for Cancer Therapy", Urban & Schwarzenberg, pp. 131-133, 1978.

Surowiec et al., "Sar Characteristics of a Dual Intracavitary Applicator for Prostate Treatment", Hyperthermia Oncology 1992, vol. 1, p. 268, 1992.

Yeh et al., "Multiple Microwave Antenna System for Prostate Cancer Hyperthermia", Hyperthermia Oncology 1992, vol. 1, pp. 269, 1992.

Camart et al., "Rectal and Urethral Applicator Association for Prostatic Gland Microwave Thermotherapy: Modelling and Experimental Results", Hyperthermic Oncology 1996, vol. 2, pp. 598-600, 1996.

Brawer, "Prostate-Specific Antigen: Current Status", CA Cancer J. Clin. 1999, vol. 49, pp. 264-281, 1999.

Oesterling, "Prostate Specific Antigen: A Critical Assessment of the Most Useful Tumor Marker for Adencarcinoma of the Prostate", The Journal of Urology, vol. 145, pp. 907-923, May 1991.

Zagars, M.D. et al., "The Prognostic Importance of Gleason Grade in Prostatic Adenocarcinoma: A Long-term Follow-up Study of 648 Patients Treated with Radiation Therapy", Int. J. Radiation Oncology Biol. Phys., vol. 31, No. 2, pp. 237-245, 1995.

Schröder et al., "Prostate Cancer Detection at Low Prostate Specific Antigen", J. Urol. 2000, vol. 163, p. 806, Mar. 2000.

Eschenbach, MD et al., American Cancer Society Guideline for the Early Detection of Prostate Cancer: Update 1997, CA Cancer J. Clin. 1997, vol. 47, pp. 261-264.

Heynick, "Radiofrequency Electromagnetic Fields (RFEMF) and Cancer: A Comprehensive Review of the Literature Pertinent to Air Force Operations", Air Force Research Laboratory (AFSC) Human Effectiveness Directorate Directed Energy Bioeffects Division, Jun. 1999.

Field et al., "An Introduction to the Practical Aspects and Clinical Hyperthermia" Tayor & Francis, pp. 263, 290, 1990.

Fenn et al., "Minimally Invasive Molopole Phased Arrays for Hyperthermia Treatment of Breast Carcinomas: Design and Phantom Tests", Presented at the 1994 International Symposium of Eclectromagnetic Compatibility, pp. 566-569, May 17-19, 1994.

Vitrogan, "Elements on Electric and Magnetic Circuits", Rinehart Press, pp. 31-34, 1971.

Gentili et al., "Two-Element Radiating System for Endocavitary Hypertermia", Hyperthermic Oncology 1988, vol. 1, pp. 904-905, Aug. 29-Sep. 3, 1988.

Barry et al., "The American Urological Association Symptom Index for Benign Prostatic Hyperplasia", vol. 148, pp. 1549-1557, Nov. 1992.

Vernon et al., "Radiotherapy with or without Hyperthermia in the Treatment of Superficial Localized Breast Cancer: Results from Five Randomized Controlled Trials", Int. J. Radiation Oncology Biol. Phys., vol. 35, No. 4, pp. 731-744, 1996.

Gustavson, "The Chemistry and Reactivity of Collagen", Academic Press Inc., pp. 211-220 (1956).

Trembly et al., "Combined Microwave Heating and Surface Cooling of the Cornea", IEEE Transactions on Biomedical Engineering, vol. 38(1):85-91, (1991).

Agah et al., "Rate Process Model for Arterial Tissue Thermal Damage: Implications on Vessel Photocoagulation", Lasers in Surgery and Medicine Wiley-Liss, Inc., vol. 15:176-184, (1994).

* cited by examiner

CATHETER

CROSS REFERENCE TO RELATED APPLICATIONS

This application is a continuation of U.S. patent application Ser. No. 10/436,500, filed May 13, 2003, which is a continuation-in-part of U.S. patent application Ser. No. 09/954,194, filed Sep. 18, 2001, now U.S. Pat. No. 6,958,075, and a continuation-in-part of U.S. patent application Ser. No. 10/247,747, filed Sep. 20, 2002, now U.S. Pat. No. 6,788,977, which is a continuation-in-part of U.S. patent application Ser. No. 09/597,234, filed Jun. 20, 2000, now U.S. Pat. No. 6,477,426. The entirety of each of these four related cases is incorporated herein by reference.

BACKGROUND OF THE INVENTION

1. Field of the Invention

The present invention generally relates to an apparatus and method for administering focused energy to a body using either a single energy applicator or multiple microwave applicators and compression of the body with a balloon filled with fluid, in order to treat visible tumors and microscopic malignant and benign cells in tissue with thermotherapy. In particular, the present invention relates to a transurethral catheter for thermal and warming therapy with compression of prostate tissue adjacent a urethra where the compression balloon is coated with a drug to create a drug-infused biological stent.

2. Description of the Prior Art

In order to treat the prostate with thermotherapy, it is necessary to heat a significant portion of the prostate gland while sparing healthy tissues in the prostate as well as the surrounding tissues including the urethral and rectal walls of a patient. The prostate gland encircles the urethra immediately below the bladder. The prostate, which is the most frequently diseased of all internal organs, is the site of a common affliction among older men, benign prostatic hyperplasia (BPH), acute prostatitis, as well as a more serious affliction, cancer. BPH is a nonmalignant, bilateral nodular tumorous expansion of prostate tissue occurring mainly in the transition zone of the prostate. Left untreated, BPH causes obstruction of the urethra that usually results in increased urinary frequency, urgency, incontinence, nocturia and slow or interrupted urinary stream.

Recent treatment of BPH includes transurethral microwave thermotherapy in which microwave energy is employed to elevate the temperature of tissue surrounding the prostatic urethra above about 45° C., thereby thermally damaging the tumorous prostate tissue. U.S. Pat. Nos. 5,330,518 and 5,843,144 describe methods of ablating prostate tumorous tissue by transurethral thermotherapy, the subject matter of which is incorporated by reference. However, improvements still need to be made in this type of therapy to further maintain or enhance the patency of the urethra after the thermotherapy treatment. In particular, urine flow is not always improved despite ablation of the tumorous tissue causing constriction of the urethra because edema produced by the transurethral thermo-therapy treatment blocks the urethra passage resulting in patients treated by the above methods to be fitted with catheters for several days or weeks after the thermotherapy treatment.

U.S. Pat. Nos. 5,007,437, 5,496,271 and 6,123,083 disclose transurethral catheters with a cooling balloon in addition to the anchoring or Foley balloon and are incorporated by reference herein. However, these patents circulate fluid, which acts as a coolant for removing heat preferentially from the non-prostatic tissue adjacent thereto, through the cooling balloons. The '083 patent further discloses the use of a thermotherapy catheter system taught by U.S. Pat. No. 5,413,588 that employs chilled water between about 12°-15° C. as the coolant. Chilled water significantly cools the urethra adjacent the cooling balloon. Likewise, the '271 patent describes a coolant as the fluid to keep the urethral wall temperatures cool. This chilling of the urethra does not aid in maintaining an opening within the heated urethra after the cooling balloon is removed, and reduces the therapeutic effect in the tissue immediately adjacent the urethral wall.

Another known alternative to thermal surgery, as described in U.S. Pat. No. 5,499,994, is to insert a dilation balloon in the urethra and to expand the dilation balloon to compress the obstructed urethra. However, the expansion of the dilation balloon occurs over 24 hours and the patient still is not cured of the diseased prostate. Further, the expansion can cause adverse effects (e.g., tearing of the urethral walls). U.S. Pat. No. 6,102,929 describes a post-operative procedure where the prostate tissue is expanded after the surgical procedure to enlarge the urethra to enable a patient to void comfortably. This expansion requires insertion of another device and requires the device to remain in the patient for a day or more.

In view of the fact that post-treatment catheters or other devices are still considered necessary by the medical community, further improvements are needed in thermotherapy to avoid the obstruction caused by edema and to maintain and enhance the opening of the urethra.

SUMMARY OF THE INVENTION

The present invention is directed to an apparatus and a method for thermally treating tissue adjacent a bodily conduit, such as a urethra, while preventing obstructions of the bodily conduit due to edema and delivering a drug or medicine to a targeted region. To achieve this object, the instant invention employs a catheter with an energy-emitting source and a compression balloon surrounding the energy-emitting source which is inflated by fluid that compresses, preps, and allows better energy coupling to the bodily conduit walls adjacent the compression balloon. The fluid inflating the compression balloon is maintained under pressure after the compression balloon is inflated to the desired diameter and, in a preferred embodiment, is not circulated so that heat is not carried away from the bodily conduit walls thereby improving the formation of the biological stent and sustaining the formation of the biological stent, especially in the area and tissue immediately adjacent to the compression balloon.

The compression balloon is coated with a drug or medicine or gene modifier, designed to aid in cancer treatment, cure infectious diseases, relieve pain, and/or to cause a stronger biological stent thus limiting the potential for restenosis. In conjunction with drug or medicine therapy, or alone, gene modifiers may coat the compression balloon for gene therapy. The heat from microwave, radio frequency, ultrasound or a like energy-emitting source, and/or light from any light emitting source, such as a laser, that is generated immediately adjacent to the coated compression balloon allow the gene modifier, drug or medicine to be effectively released, absorbed, and/or activated into the target area. The compression balloon may be coated with any of the standard cytotoxic drugs so that may be released adjacent to the target area being treated for cancer, for example. If benign conditions surrounding a bodily conduit are being treated, antibiotics or other drugs that combat one of the infectious diseases or a benign condition, such as prostititus, may coat the compression balloon. Depending upon the treatment, a general pain relief medication may be coated on the outside of the compression balloon, alone or in combination with another drug or gene modifier for a specific disease that is readily accessible via a bodily conduit.

While the instant invention will be described with respect to a preferred embodiment where the bodily conduit is the urethra and prostatic tissue is to be treated by thermotherapy, the combination of compression, an energy source such as, microwaves, radio frequency, ultrasound, heated fluid or laser, and gene or drug therapy can be used to achieve the above goal in other bodily conduits or intracavity sites including, but not limited to, cardiovascular, esophageal, nasal pharynx, and rectal cavities or organs accessible by body conduits such as lung, liver, ovaries, and etc. That is, it is a goal of the instant invention to open up bodily conduits so that the normal function of that conduit is not hampered and to treat both diseased and/or benign sites, as well as the relief of pain, by delivering applicable gene modifiers, drugs or medication to the targeted area. The power to the energy-emitting source for heat or light, and diameters and shaping of the compression balloon and catheter will vary depending upon the tissue or bodily conduit or organ to be treated and the coated material on the compression balloon.

Unlike known techniques that circulate fluid to remove heat from the urethral walls, the instant invention employs, in a preferred embodiment, low energy to heat tissue adjacent the bodily conduit walls and compression so that tissue further from the bodily conduit walls is easier to heat using a lower energy while still maintaining the temperature of the urethra above 30° C. and avoiding overheating of the urethra. The Applicant believes that the urethral wall or targeted area should not be cooled by a circulating fluid as a biological stent or molded opening would not be formed effectively with cooled circulation fluid (i.e., fluid circulated into a patient in the range of 25° C.-30° C. or lower). The lack of a circulating fluid is advantageous in that a lower energy may be used to therapeutically heat the prostate or other treatment site, as the heat is not drawn away from the treatment site when the fluid does not circulate or remains in the inflated compression balloon. Additionally, the lack of the circulating fluid does not detract from the heating and/activating or releasing of the gene modifier, drug and/or medicine disposed in the coated material on the compression balloon. While no circulation of the water is the preferred embodiment, a circulation of non-cooled fluid may also be used.

According to the exemplary invention, a select volume of collagen-containing tissue surrounding the urethra or an area immediately adjacent thereto is heated to a temperature of greater than 43 degrees C. for a time sufficient to substantially destroy or modify the select volume of tissue. Prior to energizing the energy-emitting source, a preshaped coated compression balloon is filled with fluid to expand the urethral walls compressing the prostate thereby reducing blood flow in the prostate surrounding the urethral walls and as a result, the energy-absorptive heating is more efficient in the region of constricted blood supply. The compression will also enlarge the surface area of the walls of the bodily conduit so that more drug is delivered efficiently per tissue area. In addition, compression of the area via the compression balloon could also lessen the distance from the surface of the balloon to the total targeted tissue thereby increasing the treatment zone if desired. The compression, together with the lack of a circulating fluid, theoretically enables a lower amount of energy than previously thought possible to heat the prostatic tissue or other tissues to therapeutic temperatures while causing the proteins of the urethral walls to become denatured or unraveled in the presence of the heat emitted from the energy-emitting source. That is, energy-emitting source 110 may be energized to a low power in the range of 0 watts to approximately 20 watts. Alternatively, the energy-emitting source alone may radiate heated fluid, such as water to provide the needed heat, or may be another energy source used in conjunction with heated fluid. As a result, it is envisioned that this preferred embodiment, in combination with a coated balloon, may provide a more permanent stent or a more effective treatment than thought possible with a lower treatment or release temperature, such as greater than or equal to 38 degrees C.

The fluid, which expands the compression balloon and remains inside the inflated balloon, does not detract from the denaturing process which forms the biological stent, as the fluid does not carry away heat from the urethral walls. In one aspect of this invention, the non-circulating fluid together with the material of the inflated balloon provides the ability to form a more lasting and efficient biological stent to the urethral wall or closed vesicle as the result of the heat, compression and the coated material. This invention addresses a new, improved and more effective method of thermotherapy by uniquely coating the compression balloon with a drug, gene therapy compound or other medicament, compressing the coated balloon with circulating or non-circulating fluid and activating the drug, gene therapy compound or other medicament of the coated material via either heat or light energy sources.

A second aspect of this invention is directed towards a targeted direct therapeutic delivery system with drug therapy and/or gene therapy compounds to treat the affected area. The non-circulating fluid is in direct contact with the antenna or other energy-emitting source that emits the lower energy so that it provides a better coupling of the emitted lower energy to produce heat in the compressed prostatic tissues or other tissues. This is referred to as direct coupling technology as the non-circulating fluid conducts the energy emitted from the antenna or other source to the compressed prostatic tissues. Certain applications of the low energy-emitting apparatus according to the invention are envisioned where the inflation fluid would not be in direct contact with the antenna or other source and still would provide the necessary heat or light to therapeutically treat the diseased tissue. As a result of the fluid in the compression balloon coupling the low emitted energy to the prostate and urethra, air pockets in the balloon are minimized and thus, "hot spots", which occur as a result of the air pockets, are less of a problem thereby resulting in better patient tolerance to the heat treatment and better uniform heating to the entire prostate.

The heating of the proteins of the urethral walls to more than 43° C. causes the proteins to become denatured or unraveled. The denaturing allows the urethral walls to conform to the expanded shape of the urethra created by the compression balloon and reduces the elasticity of the urethral walls so that a stent reinforcement period following the heating naturally solidifies the expanded shape resulting in a biological stent. That is, the expanded bodily conduit walls do not return to their previous shape after the compression balloon is deflated and removed thereby achieving a natural opening in the bodily conduit. The addition of a cytotoxic drug, for example, will aid to the ability in synergy with the heat or light to cause the biological stent, and/or cause activation and/or delivery of the desired drug or compound to also treat the affected tissue.

During the applications phase, a physical pulsing via compression and decompression of the compression balloon may be perform at various specified periods throughout the treatment to allow the rush of blood in and out of the compressed tissue. This physical or mechanical manipulation of the coated compression balloon also may be used in situations calling for a drug and/or a gene therapy compound so that the pulsing activates/releases the compound material applied to a patient via an intravenous or injection method so that the compound, which is dependent on heat or light for activation or release, is delivered to the targeted tissue. This mechanical compression and decompression can also aid in the mechanical fixation of the drugs and or gene therapy compounds to the targeted protein and/or DNA tissue. It is noted that this mechanical method fixation may cause the binding of the drugs and/or gene therapy compound disposed in the coated balloon to the protein and/or DNA. The resultant binding of the drug or gene therapy compound to the targeted protein and/or DNA is a major new innovation to ensure that the desired compound is effectively fixated or delivered to the targeted tissue.

According to a preferred embodiment of the invention, a stent reinforcement period of approximately up to 10 minutes or less follows the heating step. The stent reinforcement period maintains the pressure of the compression balloon after power to the energy-emitting source has been turned off so that a solidified expanded urethra is achieved minutes after thermotherapy and a catheter or other device is not necessary. The compression balloon during this reinforcement period also fixates the released drugs and/or gene therapy compounds within compressed tissue as a result of reduced blood flow.

Due to the fact that fluid is not circulated inside the balloon, the compression balloon may be made from either a compliant material, such as silicone material, or a non-compliant material, such as PET and still be easy to expand or be inflated by the fluid. In a preferred embodiment, the compression balloon is generally cylindrical with a sloped area on both sides of the compression balloon and is symmetrical along the length of the diameter according to a preferred embodiment. The position of the energy-emitting source in the preferred embodiment may be fixed. However, the compression balloon may be of any shape to create a desired mold or stent within a bodily conduit or urethra and may be asymmetrical along the length of the catheter. The use of a non-compliant material, such as PET, enables unique fixed expansion shapes to be formed when the balloon is inflated.

The compression balloon needs to maintain a pressure of about 5-25 psi against the urethral wall or other targeted tissue area along the length of the catheter with the preferred level of pressure being about 10-25 psi. Depending upon the size and shape of the compression balloon, the volume of fluid necessary to inflate or expand the balloon to its desired shape varies so that the appropriate amount of pressure is achieved in the inflated compression balloon. The compression balloon may have a variable diameter along the length of the catheter and may be formed from a single balloon or multiple balloons.

The material of the compression balloon touching the urethral wall is very thin in contrast to the thickness of a traditional low temperature catheter, which is generally 5 times the thickness of the compression balloon material or up to 1 cm. A preferred thickness of the material of the inflated compression balloon touching the urethral wall could be less than approximately 2 mm, and as a result of the compression, the transition zone between the fluid coupling and the prostatic tissue is minimized. In addition, the temperature of the fluid used to inflate the compression balloon is predetermined depending upon the application and varies over a range from about 0° to 50° C. This represents the starting temperature of the non-circulating fluid used to compress the balloon to the desired size and hardness. The fluid could be low lose or high lose depending on if the energy is to be either absorbed by the fluid or transparent through the fluid. The fluid may be heated to diffuse the energy uniformly in the bodily conduit or organ, or if a transparent fluid is employed, the heat generated by the energy-emitting source would heat the coated balloon directly and/or adjacent tissue. Again, the starting temperature of the fluid for inflating the compression balloon is dependent on the specific release and/or activation properties of the drugs and/or compounds disposed in the coated material. The beginning temperature of this fluid (before heating by the energy-emitting source) is envisioned to be from about 0 degrees to 50 degrees C.

According to the invention, a standard Foley bladder location balloon is disposed at the end of the catheter and a distal end of the compression balloon is mounted close to the neck of the Foley bladder balloon so that the distal end of the compression balloon is no greater than 2 cm away from the neck in the applications heating the prostate. For other sites, other forms of physical structures or imaging techniques are envisioned to provide direct placement to the delivery site. However, for example, in a preferred embodiment heating the prostate, the distal end of the compression balloon would be mounted within 1 cm of the bladder neck.

The energy-emitting source, such as a microwave antenna, may be mounted within the compression balloon fixedly or movably. If the energy-emitting source is movable, the maximum heating field may be moved forward or backward relative to the compression balloon. That is, the position of the energy-emitting portion can vary to optimize the heating of tissue for a particular therapy. The preferred location and movement, if any, of the energy-emitting source would depend on the size and shape of the compression balloon and the type of coated material or adjacent tissue to be treated. For example, a movable energy-emitting source (e.g., microwave antenna) could be used with compression balloons having a longer length. Alternatively, the energy-emitting source may be removable from one compression balloon and used with another compression balloon of differing length and diameter. This would provide a versatile apparatus, where the antenna can be used a multiple of times with different compression balloons. This feature together with less equipment needed to produce the thermocompression apparatus according to the invention makes the catheter apparatus easier and less expensive to manufacture.

BRIEF DESCRIPTION OF THE DRAWINGS

These and other features and advantages of the invention will be further understood from the following detailed description of the preferred embodiment with reference to the accompanying drawings in which.

DETAILED DESCRIPTION OF THE INVENTION

The present invention is directed to a device and a method for thermally treating tissue adjacent a bodily conduit, such as a urethra, while preventing obstructions of the bodily conduit due to edema and delivering a drug or medicine to a targeted region of the tissue to be treated. Examples and alternatives of the method and apparatus according to the present invention will be described and illustrated below after a brief discussion of collagen.

Collagen is a principal component of connective tissue and fibromuscular tissues. Collagen also has known properties such as plastic remodeling when subjected to high temperatures (e.g. about 60° C. to 70° C.). Specific remodeling temperatures are generally more exactly identifiable for a type and age of tissue in a particular location of the body. In the embodiment according to the invention, Applicant theorizes that the remodeling temperature is lowered as a result of the bodily conduit being reshaped and the tissue adjacent to the conduit being compressed to significantly reduce the blood flow. General principles of collagen and collagen reactivity to thermal treatment are known in the art and are described in the following articles, amongst others: Gustayson, The Chemistry and Reactivity of Collagen, Academic Press, Inc., New York, 1956, specifically including p.p. 211-220; Agah et. al., Rate Process Model For Arferial Tissue Thermal Damage: Implications on Vessel Photocoagulation, Lasers in Surgery and Medicine, 15:176-184 (1994); Trembly et. al., Combined Microwave Heating and Surface Cooling of the Cornea, IEEE Transactions On Biomedical Engineering, Vol. 38, No. 1, 1991, Stringer et. al., Shrinkage Temperature of Eye Collagen, Nature, No. 4965, pp. 1307.

Of specific interest, collagen is found in fibromuscular tissue and other interstitial connective tissue forming part of or surrounding various ducts in the body. For example, the urethra is a duct in the lower urinary tract that passes fluid from the bladder, through the prostate, and out of the body via the penis. Proximal portions of the prostatic urethra are surrounded by a ring of fibromuscular tissue and by interstitial tissue in the prostate, both types of tissue including collagen. Manipulation of this collagen in the method of the present invention is used to remedy various dysfunctions of the prostate and/or urethra, such as benign prostatic hyperplasia. Accordingly, the urethra is one example of a duct in the body having collagen rich surrounding tissue and a diameter that must be carefully controlled to maintain normal function, which is addressed by the method of the present invention.

Figure 1:
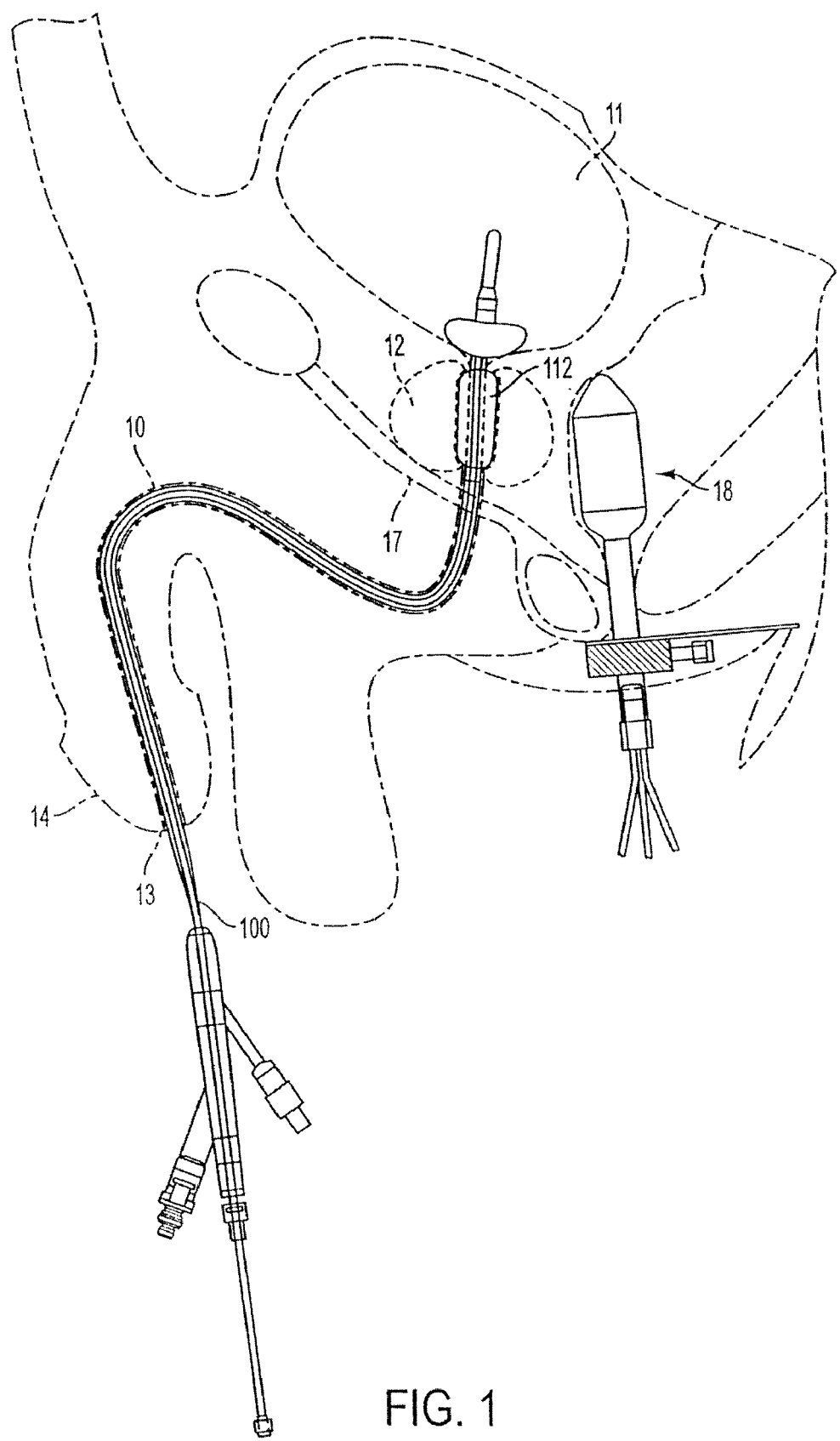
FIG. 1 is a vertical sectional view of a male pelvic region showing urinary organs affected by benign prostatic hyperplasia and an inserted catheter according to the invention with inflated compression and Foley balloons.

A method and apparatus for thermally treating tissue adjacent a bodily conduit, such as an urethra, according to the invention, delivers a gene compound or drug or medicine to a targeted tissue area and maintains the expanded diameter of the urethra into a selected urethral shape after microwave thermotherapy treatment for benign prostatic hyperplasia to restore patency to the urethra, as illustrated in FIGS. 1-6. FIG. 1 is a vertical sectional view of a male pelvic region showing the effect of benign prostatic hyperplasia (BPH) on the urinary organs. Urethra 10 is a duct leading from bladder 11, through prostate 12 and out orifice 13 of penis end 14. Benign tumorous tissue growth within prostate 12 around urethra 10 causes constriction of urethra 10, which interrupts the flow of urine from bladder 11 to orifice 13. The tumorous tissue of prostate 12, which encroaches urethra 10 and causes the constriction (not shown, as compression balloon 112 is inflated), can be effectively removed by heating and necrosing the encroaching tumorous tissue. This is accomplished, according to the invention, by inserting an energy-emitting source containing catheter 100 into a bodily conduit (e.g., urethra) so that the energy-emitting source 110 is positioned in a region of an organ (e.g., prostate) in order to radiate energy to heat the tissue to be treated adjacent the bodily conduit. Ideally, with the present invention, periurethral tumorous tissue of prostate 12 anterior and lateral to urethra 10 is heated and necrosed while avoiding unnecessary and undesirous damage to urethra 10 and to adjacent healthy tissues, such as external sphincter 17, rectum 18, and bladder neck 19.

Figure 2:
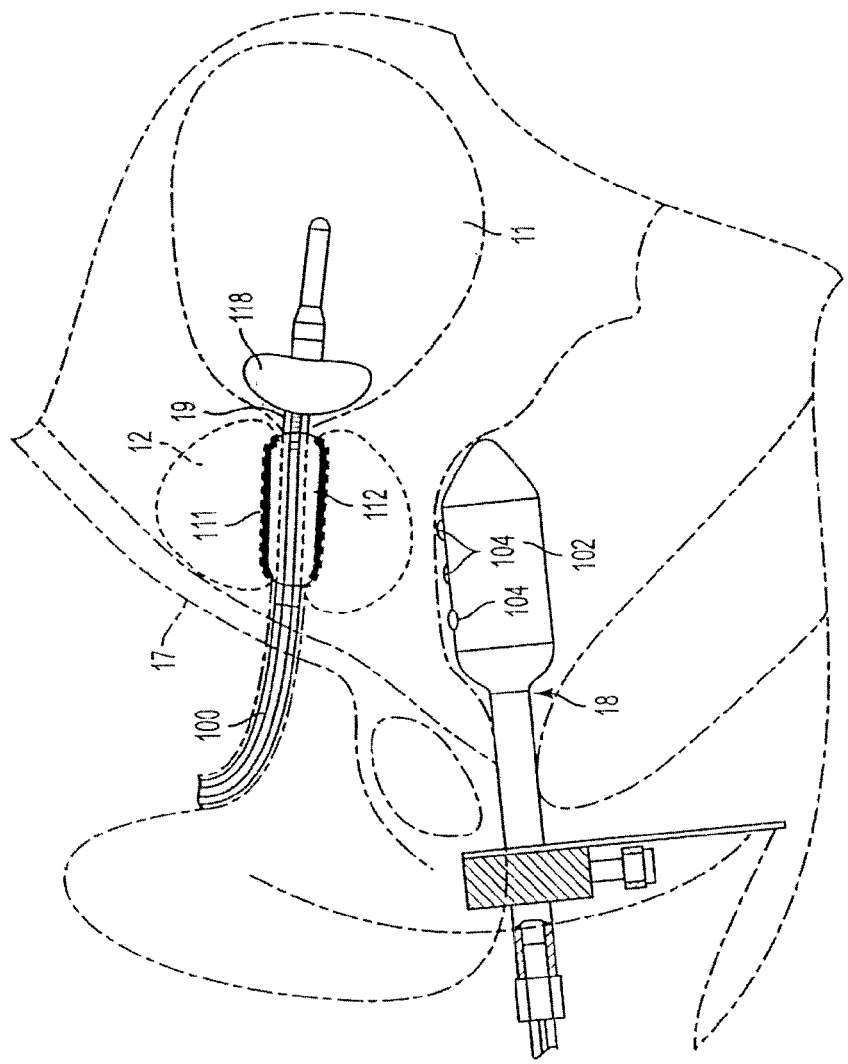
FIG. 2 is an enlarged portion of FIG. 1.

FIG. 2 is an enlarged sectional view of FIG. 1 illustrating specific anatomical features including urethra 10 and bladder 11 and showing catheter 100 with an inflated compression balloon 112 and an inflated Foley or anchoring balloon 118. As shown on FIGS. 1-4, the instant invention employs a catheter 100 with an energy-emitting source 110 and a compression balloon 112 surrounding the energy-emitting portion of source 110, which is filled with a warmed fluid to inflate the same under pressure and to maintain the warmth of the urethra walls adjacent the compression balloon. Compression balloon 112 may be coated with a material 111 including at least one gene modifier (gene therapy compound) and drug or medicine that is designed to aid in cancer treatment, cure infectious diseases, relieve pain and/or cause a stronger biological stent. A selective heating of benign tumorous tissue in prostate 12 (transurethral thermotherapy) is made possible by energy-emitting-containing catheter 100 of the present invention. The energy-emitting source 110 may produce heat from microwaves, radio frequency, ultrasound or like energy. The heat from energy-emitting source 110 and/or light from any light-emitting source, such as a laser, can activate and release the at least one gene modifier and drug or medication into the target tissue area. Thus, the heat of the energy-emitting source and/or light of a light-emitting source heats the adjacent tissue to a temperature to ablate diseased tissue and acts in synergy with coated material 111 to activate and release the gene modifier, drug or medication so that gene or drug is absorbed into the targeted tissue. A rectal probe 102 with a number of sensors is inserted into rectum 18 and measures the amount of heat generated by the absorbed emitted energy at the rectal wall.

As shown in FIG. 2, three sensors 104 are mounted on probe 102. The sensors are preferably integrally mounted at differing radial locations on the probe and spaced approximately 1 centimeter from one another. Foley balloon 118 is inserted into a patient's bladder so that the proximal end of the compression balloon is located at the patient's prostate immediately distal of the bladder neck. The length of compression balloon 112 varies depending upon the size of a patient's bladder. A typical length of the compression balloon would be about 40 millimeters and the length can range from 25 to 60 millimeters. The material 111 with at least one of a gene modifier, drug or medication coating compression balloon 112 may cover the entire length of the compression balloon to release a gene modifier, drug or medication to the adjacent tissue. In other embodiments, the coating of compression balloon 112 with material 111 may be positioned on a portion of the compression balloon so that the gene modifier, drug or medication is released to the desired target area. The compression balloon may be coated with any of the standard cytotoxic drugs used for the treatment of cancer, an antibiotic to treat a benign condition or an infectious disease, and/or pain medication used for the general relief of pain. For example, in order to treat benign prostate hyperplasia, the compression balloon 112 may be coated with a material 111 with one of Proscar, Hytrin, Flowmax, Cadora, or a drug that improves the symptoms or cures prostatic diseases. Depending upon the treatment, a general pain relief medication may be coated on the outside of the compression balloon, alone or in combination with another drug or gene modifier for a specific disease that is readily accessible via a bodily conduit.

Catheter 100 would be around 18 French (French is a measurement equal to 0.333 mm or 0.013 inch). Since the average diameter of a male adult human is about 22 French, the deflated compression balloon 112 that surrounds the catheter would add approximately 2 French so that diameter of catheter 100 and balloon 112 would be less than that of the patient's urethra for ease of insertion and less pain for the patient. Multi-lumen shaft 100 and associated molded parts are preferably extruded of a medical grade polymer sold by Concept Polymer Incorporated under the trademark C-Flex™. The compression balloon is preferably molded from a medical grade polyester material sold by Allied under the trademark PETT™, that has a limit of stretch based on its initial maximum molded shape. Alternative materials can include a silicone material manufactured by Dow Corning Inc. under the trade name Silastic R™ type Q7-4850 and type Q7-4765, for the shaft extrusion and the molded manifold, and Elastosil type LR3003/30Us for the anchoring balloon 118. The material of catheter 100 preferably has a Shore D hardness between 50 D and 80 D.

After full insertion (i.e., the deflated Foley balloon reaching into the patient's bladder), a fluid (sterile water) is pumped through the Foley inflation valve 113 thereby to inflate Foley balloon 118 and hold the catheter within the patient's urethra. Inflation valve 113 maintains fluid in the Foley balloon with the desired pressure so that the catheter is anchored in the patient. However, the catheter is still capable of limited longitudinal movement with respect to the urethra. After Foley balloon 118 has been inflated, a warmed fluid, preferably a low-loss liquid (e.g., deionized or sterile water), is slowly pumped through the one or more catheter inflation/ circulation lumens 120 (FIG. 3a) into the prostate compression balloon 112 to inflate the same expanding the urethral walls and maintaining the temperature of the urethral walls above 30° C. The diameter of the inflated compression balloon would be approximately in the range of 25-60 French, preferably in the range of about 40-60 French. Approximately 20-30 cc of fluid should fill compression balloon 112 so that its outer surface expands the bodily conduit. The warmed fluid used to inflate compression balloon 112 is preferably a minimally energy absorptive solution which conducts microwaves to the tissue to be heated more efficiently. Thus, the fluid which fills compression balloon 112 serves to compress and prep the bodily conduit and adjacent tissue surrounding the bodily conduit prior to energizing the energy-emitting source 110. In addition, the fluid provides means to couple the emitted energy to the bodily conduit walls adjacent the compression balloon to provide a more efficient heating of the tissue. Depending upon the application and the gene modifier and/or drug to be released from the coated material 111, the fluid may be a high-lose liquid or a low-lose liquid to either diffuse the heat or light or act transparent so that the heat or light is effectively delivered to release and/or activate the coated material in an efficient and uniform manner.

Figure 3:
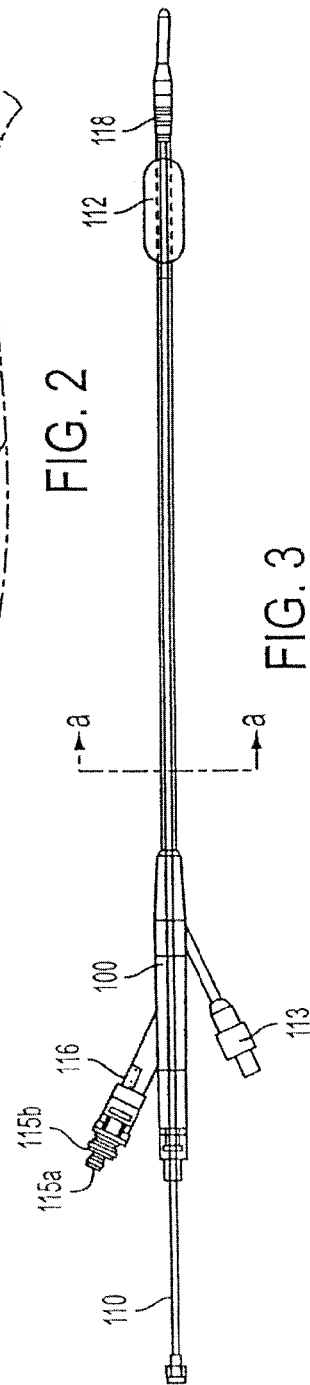
FIG. 3 is a plan view of the urethral catheter of the present invention.
Figure 3A:
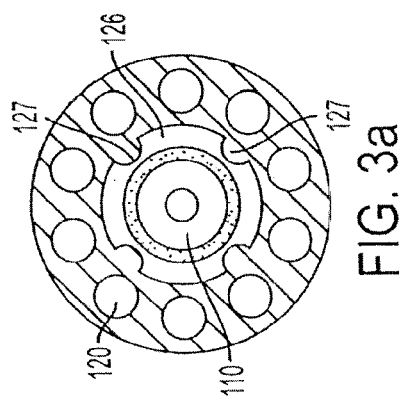
FIG. 3a is a cross-sectional view of the urethral catheter of FIG. 3 taken along line a-a.

A typical implementation of a catheter according to the invention is shown in FIG. 3. Foley balloon 118 is deflated in this Figure. As shown on the left-hand side of the Figure, a Foley inflation valve 113, a warmed, sterile-fluid intake 115a and a sterile-fluid outtake 115b are provided to receive fluid. The sterile-fluid intake and outtake 115a, 115b enable the circulation of sterile fluid in the compression balloon, if desired, during thermotherapy and maintain the desired pressure to achieve the specific fluid flow pattern and distribution of fluid within the balloon. In an embodiment where circulation of the fluid is not desired, fluid may enter fluid intake 115a and valves known to those skilled in the art and may maintain the desired pressure of the fluid filled in the compression balloon. After the stent reinforcement period described below, the fluid may be removed from the compression balloon via outtake 115b. A central lumen 126 receives the energy-emitting source 110, which may be an antenna in the form of a coaxial cable. As shown in FIG. 3a, protrusions 127 are formed in central channel 126 in order to keep energy-emitting source 110 centralized inside catheter 100 and to create channels for the removal of the filled fluid. Protrusions 127 enable the distance between the energy-emitting source and outside wall of the catheter to remain constant thereby ensuring a consistent heating pattern at the energy-emitting portion of the source 110. The energy emitting source 110 is directed coupled to the low-loss liquid to maximize emitted power and to cool the shaft of the energy-emitted source.

Figure 3B:
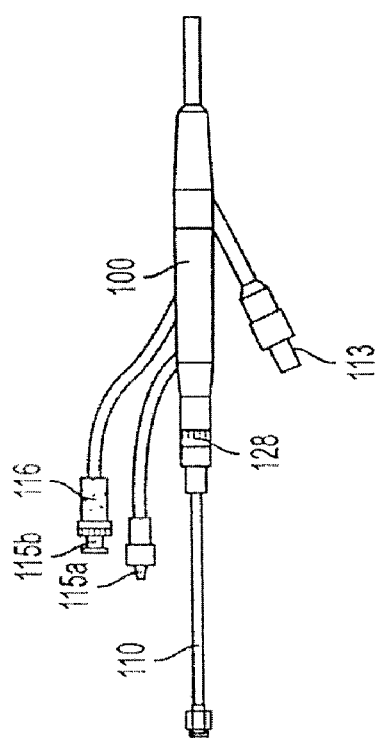
FIG. 3b shows an embodiment of a restrictive orifice of the urethral catheter of FIG. 3.
Figure 4:
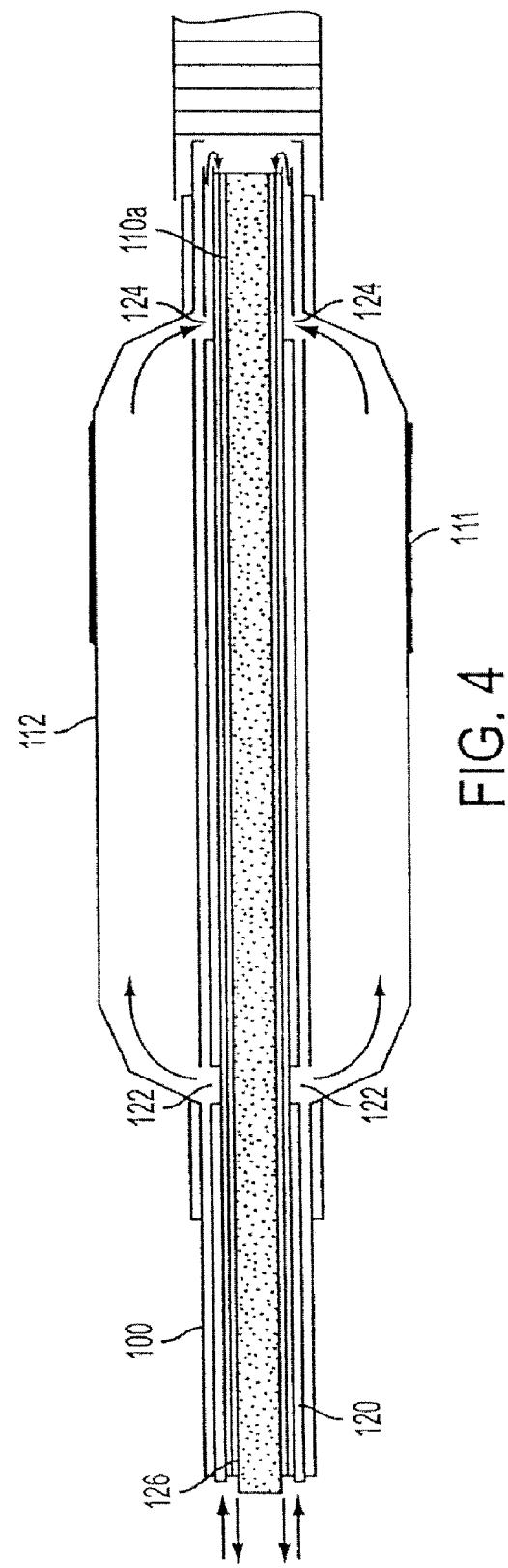
FIG. 4 illustrates the inflation of the compression balloon.

As shown in FIG. 4, orifices 122, 124 are employed in one or more of catheter lumens 120 on both sides of compression balloon 112 so that warmed fluid can be pumped through lumens 120 into compression balloon 112 at one end to fill the same and pumped out at the other end to remove the fluid. In one embodiment, the warmed water may be circulated into lumens 120, pumped into compression balloon 112 to fill the same and exit through central orifice 126, which holds an energy-emitting source 110, such as a microwave antenna to flow out of catheter 100 external of a patient. The placement and diameter of the orifices 122, 124 enables sufficient fluid flow, if desired, and pressure of about 10-25 psi to be maintained in compression balloon 112 during the entire thermotherapy treatment. In a preferred embodiment, an outtake-fluid-side channel is fitted with a restrictive orifice 116 to control the compression balloon pressure so that the compression balloon may be filled with the incoming fluid under the appropriate pressure. If no flow of the fluid pumped into compression balloon 112 is desired, a valve of the restrictive orifice 116 may act as a stopper plug, or, if some fluid flow is desired, the valve may be opened to determine the amount of fluid flow. The restrictive orifice 116, in an alternative embodiment, can be located immediately external to the catheter in the connective tubing (e.g., 115a, 115b) used to connect the catheter to the external fluid warming pumping system (FIG. 3b). The pressurization of the warmed fluid filled in the compression balloon 112 is such that air pockets are reduced in the inflated balloon. Accordingly, air pockets in the compression balloon, which may result in "hot spots" causing burns on the urethral walls, are avoided. This results in the desired compression of the prostatic urethral tissue, without burning the urethral walls, which is maintained during and after the thermotherapy treatment.

It is desired to heat the diseased prostate tissue to a therapeutic temperature (greater than about 43° C.) while maintaining the temperature of the non-prostate tissue lining the urethra above 30° C. The non-prostate tissue includes the urethral wall and adjacent tissue and is disposed between the energy-emitting source 110 and prostatic tissue 12. According to the invention, the energy-emitting source 110 is energized or activated to heat a portion of the tissue to be treated that surrounds the bodily conduit to a temperature of about 43° C. or lower depending upon the coated balloon and treatment to be performed. The tissue is heated to the determined temperature for a time sufficient to destroy a heated portion of the tissue to be treated via the heat generated by the energy-emitting source. The energy-emitting portion 110a of source 110 is disposed in catheter 100 so that it rests within the compression balloon 112. Energy-emitting portion 110a preferably emits an irradiating microwave field, which varies as an inverse function (e.g., inverse square) of the distance between the energy-emitting portion 110a (e.g., microwave antenna) and the tissue to be heated. Consequently, the non-prostatic tissue of urethral wall 10, which is closer to energy-emitting portion 110a than prostatic tissue 12, would be heated to a higher temperature than the prostatic tissue to be treated. Likewise, proximate prostatic tissue would be heated to a higher temperature than more distal prostatic tissue. Upon completion of the time sufficient to destroy a diseased or targeted tissue area, the generation of heat by energy-emitting source 110 is terminated.

U.S. Pat. No. 5,007,437 to Sterzer discloses the use of a balloon to compress the prostate tissue and to move the urethral wall away from the microwave antenna, which produces the heat. This method reduced the microwave field intensity and the resultant heat produced at the urethral wall by moving the urethral wall further from the heat-producing antenna. However, Sterzer also employed a circulating fluid to continuously cool the urethral wall while the urethral wall was inflated. Applicant recognized that this circulating coolant was preventing the urethral wall and adjacent prostatic tissue from reaching a temperature sufficient to denature the protein or enable plastic remodeling. As a result, Applicant theorized that the use of an inflated prostate compression balloon together with the circulation of warmed fluid would mitigate the denaturing problem, as shown in FIGS. 5a and 5b.

Figure 5A:
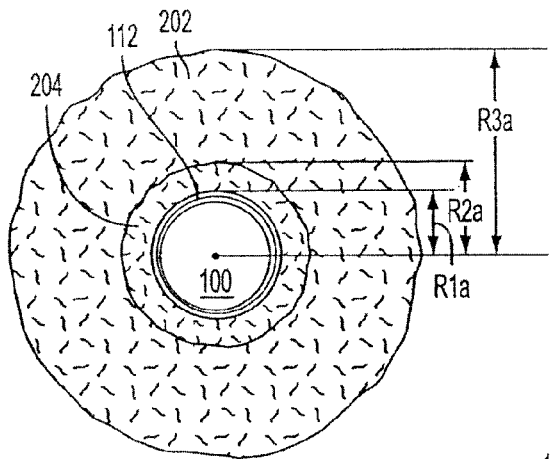
FIGS. 5a and 5b are schematic, cross-sectional views of a urethra showing the compression balloon in the uninflated and inflated states, respectively to illustrate the expansion of the urethral walls and prostate according to the invention.
Figure 5B:
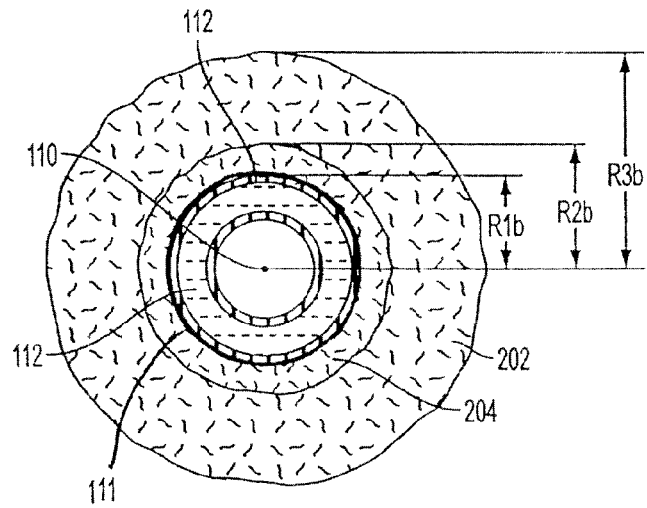

FIGS. 5a and 5b respectively show a cross-section of a deflated compression balloon and a cross-section of an inflated compression balloon. The radial distances from energy-emitting source 110, for example a microwave antenna, to distal prostatic tissue 202 and proximal tissue 204, which includes the urethral wall and adjacent non-prostatic tissue, when compression balloon 112 is deflated are smaller than those distances are when compression balloon 112 is inflated. As shown, inflated compression balloon 112 forms a symmetrical toroid extending around the entire circumference of the urethral catheter. Specifically, the radial distance $R_{1b}$ from energy-emitting source 110 to the inner circumference of proximal tissue 204 with inflated compression balloon 112 is significantly larger than the corresponding radial distance $R_{1a}$ with deflated compression balloon 112. Similarly, the radius $R_{2b}$ to the inner circumference of prostate tissue 202 with inflated compression balloon 112 is significantly larger than the corresponding radial distance $R_{2a}$ with deflated compression balloon 112. Because prostate tissue is soft and compressible, the difference between the outer and inner radii $R_{ab}$ and $R_{2b}$ of prostate tissue 202 with inflated compression balloon 112 is substantially reduced with respect to the corresponding difference between radii $R_{1a}$ and $R_{2a}$ with deflated compression balloon 112.

Consequently, the inflated compression balloon causes the prostate 12 to be compressed from the urethral wall thereby decreasing the thickness of the tissue between the compressed wall of the urethra and the margins of the prostate capsule. Consequently, the distance between the medicated coating 111 of compression balloon 112 and the targeted tissue area may be reduced thereby increasing the treatment zone. The more distal tissue 202 is not as compressed as the tissue more proximal to the urethra 204. Since the actual tissue thickness through which the energy emitted by the energy-emitting source 110 is less, the energy deposited is more evenly distributed throughout the entire prostate capsule. This makes it possible to heat the prostatic tissue more evenly and to higher therapeutic temperatures without heating any part of the non-prostatic tissue beyond its maximum safe temperature. This can be achieved with lower energy levels being emitted from the energy-emitting source 110 than previously thought possible. In addition, the compression of the tissue surrounding the inflated compression balloon in a bodily conduit enlarges the surface area that the coated compression balloon come into contact with thereby efficiently delivering more gene or drug per tissue area.

At the same time the inflated compression balloon 112 constricts the blood flow in the compressed prostate so that the irradiated heat is not carried away by the natural blood flow and thus makes this tissue more susceptible to heating by the emitted energy. Since the overall tissue thickness is reduced, the amount of energy required to effectively heat the prostate tissue 204 to a therapeutic temperature is reduced. Conversely, in typical non-compressed therapies, the amount of energy required to raise the temperature of the more distal prostatic tissue 202, that may be adjacent to the rectal wall to a maximize safe temperature of 41° C. will be significantly higher than that required according to the invention. Thus, it is possible to heat the prostatic tissue more evenly and to higher temperatures without heating any part of the non-prostatic tissue beyond its safe maximum temperature.

In order to heat proximal tissue 204 above a predetermined collagen transition temperature during a microwave thermotherapy treatment, warmed fluid above 30° C., preferably in the range of about 31° C.-60° C., fills compression balloon 112, in contrast to a coolant. As a result, the urethral wall and adjacent tissue are maintained at a temperature so that they are sufficiently denatured and a natural biological stent can be formed in the bodily conduit and adjacent tissue after the thermotherapy treatment.

The warming of the urethral wall above 30° C. and maintaining of this temperature serves to denature the proteins of the urethral wall; but does not heat the urethral wall beyond a maximum safe temperature. This denaturing allows the urethral walls to conform to the expanded shape of the urethra created by compression balloon 112 and reduces the elasticity of the urethral walls so that a stent reinforcement period following the heating of the thermotherapy treatment naturally solidifies the expanded shape resulting in a biological stent. That is, the expanded urethral walls do not return to their previous shape after the compression balloon is deflated and removed thereby achieving a natural opening in the a bodily conduit, such as a urethra.

The stent reinforcement period that follows the termination of the heating of the prostatic tissue requires that the compression balloon remain inflated at the desired pressure of 10-25 psi for up to about 10 minutes. During this reinforcement period, the pressure of the filled fluid in the compression balloon should be maintained in order to solidify the biological stent. In addition, the pressurized compression balloon during this reinforcement period can fixate the released drugs and/or gene therapy drugs compounds within the compressed tissue as a result of the reduced blood flow. That is, the stent reinforcement period maintains the pressure of the compression balloon after power to the energy-emitting source has been turned off so that drugs and/or gene therapy compounds released from the coated compression balloon fixate in a targeted tissue area and a solidified expanded urethra is achieved minutes after thermotherapy so that a urine drainage catheter or other device is not necessary.

During the stent reinforcement period, additional heat may be applied to compression balloon 112 to aid in the activation and release of the gene compounds and/or drugs in material 111 coating the outside of balloon 112 and the absorption of one the gene compounds or drugs into the targeted tissue area. The additional heat may be delivered to the compression balloon via one of hot water, radio-frequency, laser, microwave, ultrasound and infrared. It is envisioned that the additional energy may be applied to the tissue from outside of the bodily conduit. Applicant theorizes that the additional heat may result in a long-lasting or sustained biological stent being formed. The step of applying additional heat either alone or in conjunction with an appropriate, intravenously injected drug may provide pain relief, reduction of lesions and the healing of diseased tissue.

Figure 6:
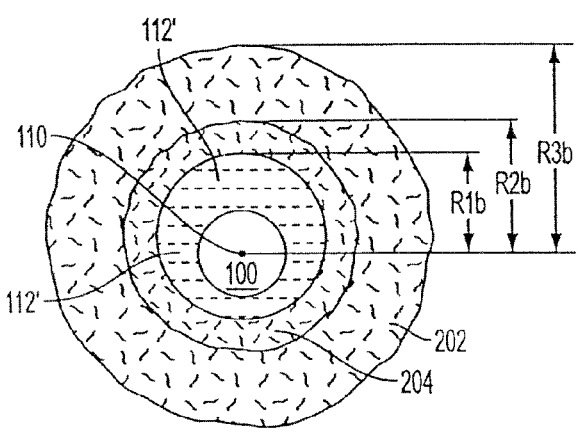
FIG. 6 is a schematic cross-sectional view of the urethra illustrating an inflated, asymmetric compression balloon according to the invention.

Compression balloon 112 is generally cylindrical with a sloped area on both sides of the compression balloon and is symmetrical along the length of the diameter according to a preferred embodiment. However, compression balloon 112 may be of any shape to create a desired mold or stent within a bodily conduit or urethra. As shown in FIG. 6, the compression balloon 112' on catheter 100 is designed so that it inflates asymmetrically around catheter 100. The asymmetrical balloon 112' inflates a bodily conduit so that a region of tissue adjacent the bodily conduit receives more or less radiate energy from the energy-emitting source 110 depending upon the width of the inflated compression balloon 112'. The wider the inflated compression balloon, the more compressed the tissue adjacent the bodily conduit becomes and the adjacent tissue is moved further from the heat producing source. It is envisioned that a coated, compression balloon inserted into a bodily conduit other than a prostatic urethra the bodily conduit is other than a prostatic urethra and the inflated compression balloon may be expanded to a diameter that is up to five times greater than a diameter of the bodily conduit in its normal and functioning size.

Compression balloon 112 preferably should be maintain about 10-25 psi against the urethral wall along the length of the catheter with the preferred level of pressure being about 15 psi. However, depending upon the size and strength of the bodily conduit, the compression balloon may be inflated to a pressure lower than or greater than the preferred range for a prostatic urethra. In another embodiment, compression balloon may be mechanically manipulated so that alternating compression and decompression of the compression balloon occurs against the bodily conduit to be treated so that at least one of a gene modifier, and a drug or medication of coated material 111 is effectively delivered and fixated to a target area of the tissue to be treated. That is, the act of compression and decompression physically manipulates the bodily conduit against the coated material 111 causing a released gene modifier or drug to fixate to a targeted area. The act of compression or decompression of compression balloon 112, which is coated with material 111, may cause the binding of the at least one of a gene modifier and a drug or medication to protein or DNA of the bodily conduit wall and/or adjacent tissue.

In another aspect of the invention, a gene modifier or a drug or medication may be injected intravenously into tissue to be treated by thermotherapy. The injected gene modifier or drug or medication can be intravenously injected adjacent the target area of diseased tissue so that a targeted direct therapeutic delivery system efficiently delivers the gene compound or medication to the affected area. It is envisioned that this direct therapeutic delivery system may be employed with a heat alone or a heat plus compression thermotherapy treatment. Of course, a compression balloon with coated material may be used in a heat plus compression thermotherapy treatment if additional gene compounds or medication is desired to be delivered to the targeted tissue area.

Although the present invention has been described with reference to preferred embodiments, workers skilled in the art will recognize that changes may be made in form and detail without departing from the spirit and scope of the invention.

I claim:

1. Apparatus for treatment of tissue within a body requiring thermotherapy, comprising:
    a catheter to be inserted into a bodily conduit, the catheter defining a central channel;
    an energy-emitting source disposed in the central channel of the catheter;
    a compression balloon including a gene modifier or a drug disposed on at least a portion of the outside of the compression balloon; and
    an external fluid warming pumping system coupled to the catheter, the catheter configured such that the compression balloon is inflated with a warmed fluid that flows from the external fluid warming pumping system, through at least a portion of the catheter and into the compression balloon and then out of the compression balloon into the central channel where the energy-emitting source is disposed, the warmed fluid being at a temperature in the range of approximately 30° C. to approximately 60° C.

2. The catheter of claim 1 wherein the energy-emitting source is configured to radiate energy.

3. The catheter of claim 2 wherein the radiated energy activates and releases the material.

4. The catheter of claim 1 wherein the catheter is configured for insertion into a bodily conduit.

5. The catheter of claim 4 wherein the bodily conduit is a prostatic urethra.

6. The apparatus of claim 1 further comprising an anchoring balloon disposed near a distal end of the catheter.

7. The apparatus of claim 1 wherein the compression balloon is coated along its entire length with the gene modifier or the drug.

* * * * *